United States Patent
Schellenberger et al.

[11] Patent Number: 6,027,873
[45] Date of Patent: Feb. 22, 2000

[54] MULTI-THROUGH HOLE TESTING PLATE FOR HIGH THROUGHPUT SCREENING

[75] Inventors: Volker Schellenberger, Palo Alto; Amy Deming Lui, Mountain View, both of Calif.

[73] Assignee: Genencor International, Inc., Palo Alto, Calif.

[21] Appl. No.: 09/272,122

[22] Filed: Mar. 19, 1999

[51] Int. Cl.$^7$ .................................................. C12Q 1/00
[52] U.S. Cl. ........................... 435/4; 435/283.1; 435/29; 435/30; 422/50; 422/68.1
[58] Field of Search .............................. 435/4, 283.1, 29, 435/30; 422/50, 68.1

[56] References Cited

U.S. PATENT DOCUMENTS

| | | | |
|---|---|---|---|
| 4,493,815 | 1/1985 | Fernwood et al. | 435/4 |
| 4,834,946 | 5/1989 | Levin | 435/4 |
| 5,000,921 | 3/1991 | Hanaway et al. | 435/4 |
| 5,047,215 | 9/1991 | Manns | 435/4 |
| 5,108,704 | 4/1992 | Bowers et al. | 435/4 |
| 5,210,021 | 5/1993 | Goodwin, Jr. | 435/4 |
| 5,262,128 | 11/1993 | Leighton et al. | 435/4 |
| 5,284,753 | 2/1994 | Goodwin, Jr. | 435/4 |
| 5,506,141 | 4/1996 | Weinreb et al. | 435/4 |
| 5,560,811 | 10/1996 | Briggs et al. | 435/4 |
| 5,770,440 | 6/1998 | Berndt | 435/4 |

*Primary Examiner*—Louise N. Leary
*Attorney, Agent, or Firm*—Nixon Peabody LLP

[57] ABSTRACT

A method for holding samples for analysis and an apparatus thereof includes a testing plate with a pair of opposing surfaces and a plurality of holes. Each of the holes extends from one of the opposing surfaces to the other one of the opposing surfaces. The holes are arranged in groups, where each group has at least two rows and two columns of holes. The groups are arranged in sets, where each set has at least two rows and two columns of groups. To analyze samples, at least one of the opposing surfaces of the testing plate is immersed in a solution to be analyzed. A portion of the solution enters openings for each of the holes in the immersed opposing surface. Once the holes are filled with solution, the testing plate is removed and is held above a supporting surface. Surface tension holds the solution in each of the holes. The solution in one or more of the holes is then analyzed and the solution in one of these holes is identified for further study. The location of the identified solution is marked based upon its location within a particular set and group of holes.

31 Claims, 5 Drawing Sheets

MULTI-THROUGH HOLE TESTING PLATE FOR HIGH THROUGHPUT SCREENING

FIELD OF INVENTION

This invention is related generally to a testing apparatus and, more particularly, to a multi-through hole testing plate for high throughput screening.

BACKGROUND OF THE INVENTION

Prior testing apparatuses have consisted of a testing plate with a pair of opposing surfaces and a plurality of wells. The wells extend in from one of the opposing surfaces, but do not extend through to the other opposing surfaces. The wells are used to hold samples of solution to be analyzed.

Although these testing apparatuses work there are some problems. For example, the wells in these testing apparatuses are difficult to fill. Special delivery systems, such as large pipette systems, are needed to fill each of the wells with samples of solution. These special delivery systems are often expensive and difficult to operate. As a result, the overall cost of the testing procedure is increased.

Another problem with these prior testing apparatuses is with their construction. The bottom of the wells in these testing plates need to be transparent so that light can be transmitted through the samples during testing. However, the rest of the testing plate needs to be constructed of a non-transparent material. The construction of a testing apparatus with these characteristics is difficult and expensive.

Yet another problem with these prior testing apparatuses is with the operator locating a particular well in the testing apparatus. Typically, these testing apparatuses each include large numbers of wells which are equidistantly spaced apart. As a result, locating a particular well within the large number of wells is difficult.

Accordingly, there is a need for an improved testing apparatus for high throughput screening.

SUMMARY OF THE INVENTION

A method for holding samples in accordance with one embodiment of the present invention includes several steps. First, a testing plate with a pair of opposing surfaces and a plurality of holes is provided. Each of the holes extends from one of the opposing surfaces to the other one of the opposing surfaces. Next, at least one of the opposing surfaces of the testing plate is immersed in a solution to be analyzed. A portion of the solution enters openings for each of the holes in the immersed opposing surface and any gases in the holes escape through openings for each of the holes in the other opposing surface. Next, the testing plate is removed from the solution. Surface tension holds some of the solution in each of the holes. The opposing surfaces of the testing plate are then held above a supporting surface and the solution held in at least one of the holes is analyzed.

A method for identifying the location at least one sample of a solution in accordance with another embodiment of the present invention includes several steps. First, a testing plate with a pair of opposing surfaces and a plurality of holes is provided. Each of the holes in the testing plate extend from one of the opposing surfaces to the other one of the opposing surfaces. The holes in the plate are arranged in groups. Each of the groups comprises at least two rows and two columns of holes. Once a testing plate has been provided, solution is loaded into the holes and is then analyzed. Based on this analysis, the solution in at least one hole is identified for further study. The location of the identified hole is marked based upon the group in which the hole is found.

A method for screening a sample in accordance with another embodiment of the present invention includes several steps. First, a solution of the sample is prepared for screening. Next, a testing plate with a pair of opposing surfaces and a plurality of holes is provided. Each of the holes extends from one of the opposing surfaces to the other one of the opposing surfaces in the testing plate. Next, at least one of the opposing surfaces of the testing plate is immersed in a solution. A portion of the solution enters openings for each of the holes in the immersed opposing surface of the testing plate. Once the solution has enter into the holes, the testing plate is removed from the solution and the surface tension holds at least some of the solution in the holes. Next, the solution in one or more of the holes is analyzed.

An apparatus for holding samples of a solution with cells for analysis in accordance with another embodiment of the present invention includes a testing plate with a pair of opposing surfaces and a plurality of through holes. Each of the holes extends from an opening in one of the opposing surfaces in the testing plate to an opening in the other one of the opposing surfaces and is sized to hold a plurality of the cells. A portion of at least one of the opposing surfaces of the testing plate where the holes are located is recessed so that the openings in the testing plate are spaced in from the opposing surface.

An apparatus for holding samples for analysis in accordance with yet another embodiment of the present invention also includes a testing plate with a pair of opposing surfaces and a plurality of holes. Each of the holes extends from one of the opposing surfaces to the other one of the opposing surfaces. The holes are arranged in groups on the testing plate, where each of the groups comprises at least two rows and two columns of holes.

The method and apparatus for holding samples for analysis in accordance with the present invention provides a number of advantages. For example, the present invention simplifies testing procedures. The samples of solution to be analyzed can be loaded into the testing plate by simply dipping or flooding one of the surfaces of the testing plate into the solution. As a result, the present invention does not require the use of a separate delivery systems for loading solution into the wells on the testing plate.

The present invention also simplifies the construction of the testing apparatus. The testing apparatus merely needs one of the opposing surfaces of the testing apparatus to be spaced away by additional spacers or machined to create a recessed portion and then a plurality of holes need to be drilled through the plate in the recessed portion. Unlike prior testing apparatuses, the present invention does not require any special construction techniques to make the bottom of the wells transparent because the holes extend all of the way through the plate.

The present invention also permits an operator to more easily identify a particular hole filled with a sample for further analysis. Instead of spacing the holes equidistantly over the testing plate, the present invention arranges the holes in groups of at least two columns and two rows of holes and arranges the groups in sets of at least two or more. The groups are spaced further apart then the holes within each group and the sets of groups are spaced further apart then the groups are spaced apart. As a result, an operator can more easily identify a particular hole based upon which set, group, row, and column the hole is located in on the testing plate.

DETAILED DESCRIPTION

Figure 1:
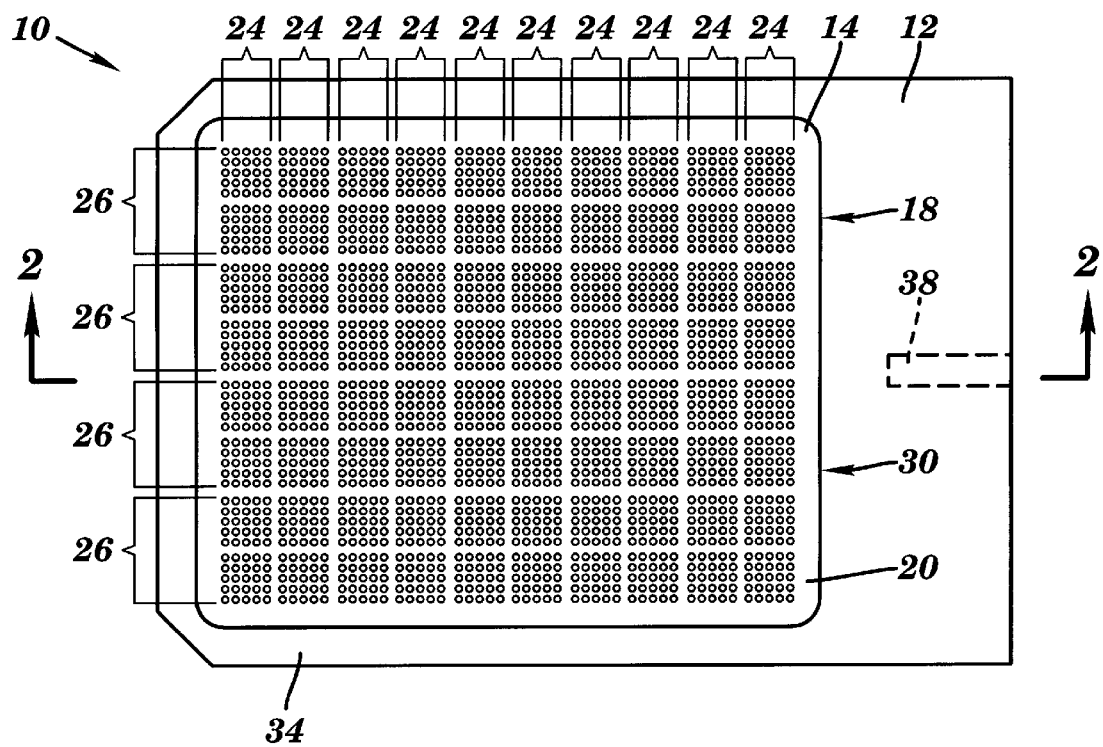
FIG. 1 is a top view of a multi-through hole testing plate in accordance with one embodiment of the present invention.
Figure 2:
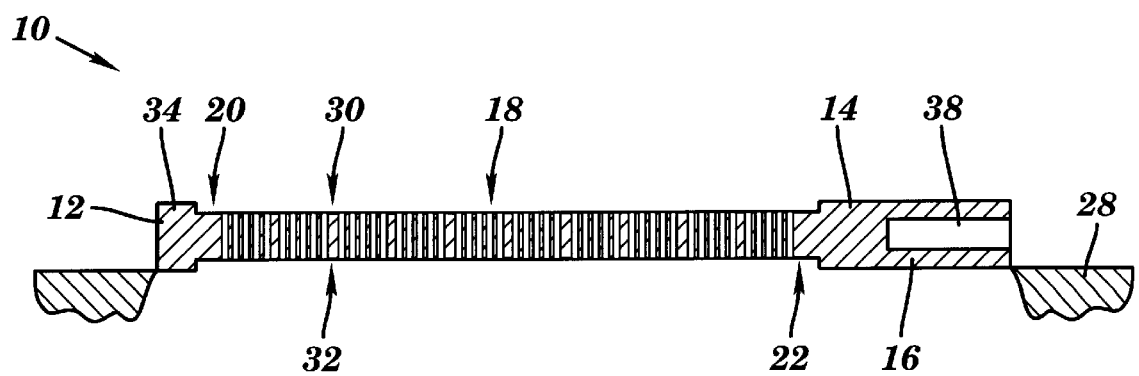
FIG. 2 is a cross-sectional view of the multi-through hole testing plate shown in FIG. 1 taken along lines 2—2.

A testing apparatus 10 in accordance with one embodiment of the present invention is illustrated in FIG. 1. The testing apparatus 10 includes a testing plate 12 with a pair of opposing surfaces 14 and 16 (surface 16 is shown in FIG. 2) and a plurality of through holes 18. The through holes 18 are located in recessed portions 20 and 22 on each side of the testing plate 12. The through holes 18 are also arranged in groups 24 of at least two columns and two rows of holes 18 and in sets 26 of two or more groups of holes 18. The testing apparatus 10 provides a number of advantages including simplifying the procedure for loading samples of solution S into the holes 18 in the testing apparatus 10, simplifying the construction of the testing apparatus 10, and making the identification of a particular hole 18 filled easier for an operator.

Referring to FIGS. 1 and 2, the testing apparatus 10 includes the testing plate 12 which in this particular embodiment is made of a non-transparent material, such as aluminum and polypropylene, although other types of materials, such as teflon, polystyrene, stainless steel, polyethylene, any metal or plastic, can be used. The testing plate 12 could also be made of transparent materials, such as glass or transparent plastic, when non-optical means are used for analysis, such as analyzing the materials blotted on membranes.

The testing plate 12 includes the pair of opposing surfaces 14 and 16. In this particular embodiment, the opposing surfaces 14 and 16 are substantially planar, except where the recessed portions 20 and 22 are located, although the surfaces 14 and 16 could have other relationships with respect to each other. Each of the opposing surfaces 14 and 16 includes one of the recessed portions 20 and 22 which are machined into the testing plate 12, although other techniques for forming the recessed portions 20 and 22, such as by molding or adding spaces, can be used. When either of the opposing surfaces 14 and 16 of the testing plate 12 rests on a supporting surface 28, the recessed portion 14 or 16 along with the plurality of holes 18 located in the recessed portion 14 or 16 are spaced away from the supporting surface 28. If openings 30 and 32 to the holes 18 contacted the supporting surface 28, then any solutions in the holes 18 would drain out of the holes 18. In this particular embodiment, a ridge 34 if formed in each of the opposing surfaces 14 and 16 by the recessed portions 20 and 22 which extends around the outer circumference of the testing plate 12. Although the holes 18 are spaced from the support surface 28 by a recessed portion 20 or 22 formed in the testing plate 12, the holes 18 can be spaced from the supporting surface 28 with other types of supporting structures, such as a bracket attached to the testing plate which supports the testing plate 12 and holes 18 above the supporting surface 28.

Figure 5:
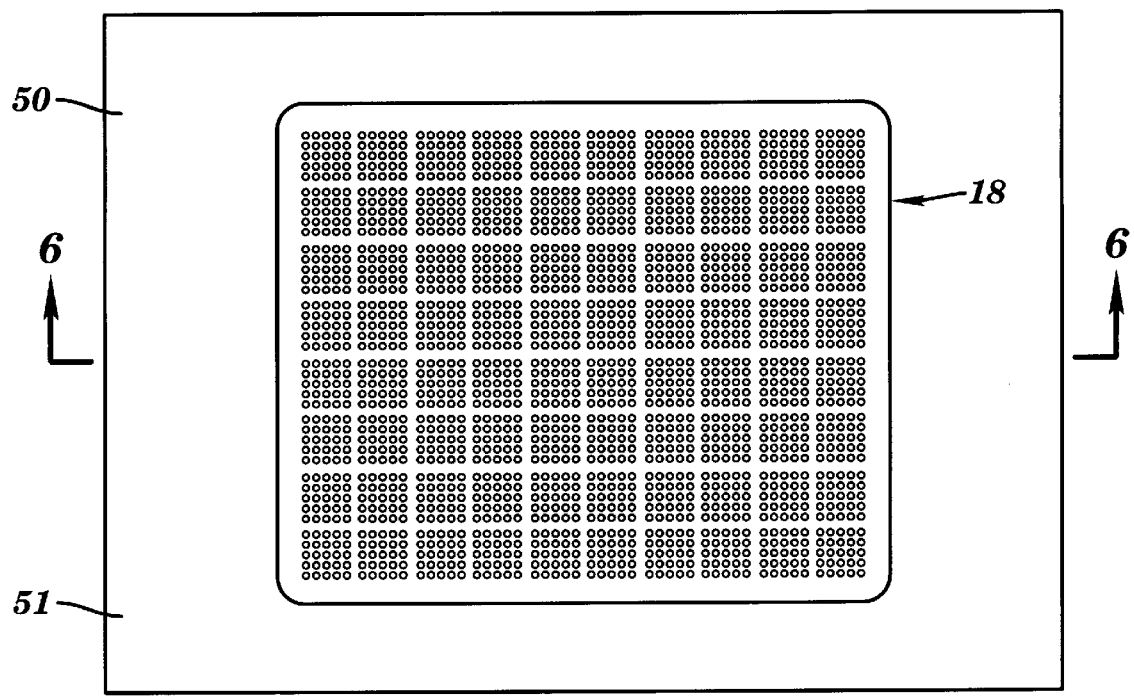
FIG. 5 is a top view of the multi-through hole testing plate in accordance with another embodiment of the present invention.
Figure 6:
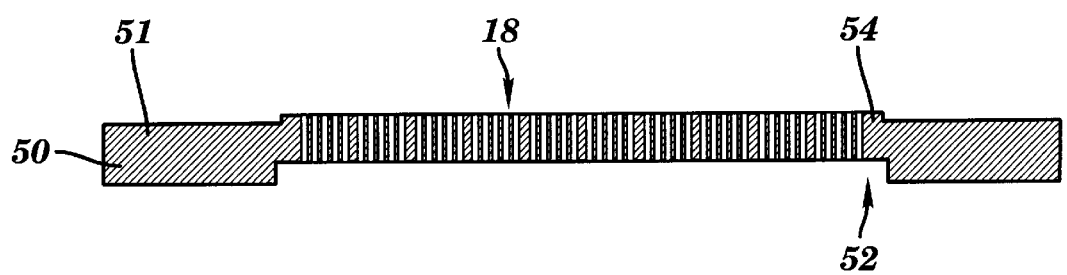
FIG. 6 is a cross-sectional view of the multi-through hole testing plate shown in FIG. 5 taking along the lines 6—6.

Referring to FIGS. 5 and 6, another testing apparatus 50 in accordance with one embodiment of the present invention is illustrated. The testing apparatus 50 is identical to the test apparatus 10 shown in FIGS. 1 and 2 except that the testing apparatus 50 does not include a pair of recessed portions. Instead, the testing apparatus 50 has a recessed portion 52 and a protruding portion 54. When the testing plate 51 is placed on a supporting surface, the recessed portion 52 must be facing the supporting surface so that the holes are spaced from the supporting surface. Although one example of the testing apparatus 50 is shown, the opposing surfaces of the testing plate 51 could have other configurations. For example, protruding portion 54 could be made flush with the upper surface of testing plate 51.

Figure 3:
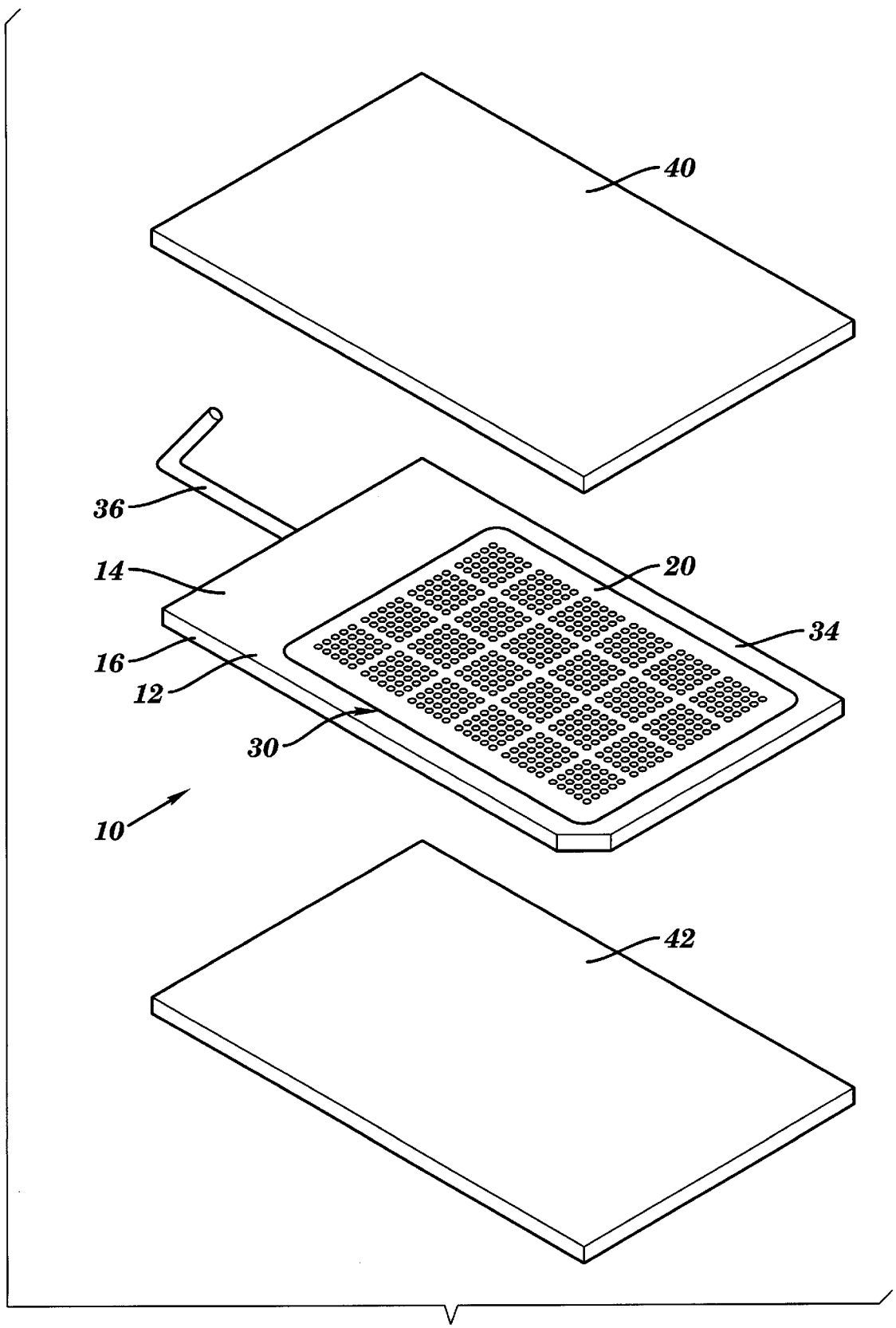
FIG. 3 is a perspective, exploded view of another multi-through hole testing plate in accordance with the present invention between a pair of evaporation plates.

Referring to FIGS. 1–3, the testing plate 12 also includes an optional handle 36 and an opening 38 on one side of the testing plate 12 to receive one end of the handle 36, although other techniques for connecting the handle 36 to the testing plate 12 can be used, such as connecting the handle 36 with bolts. The handle 36 extends out from the side of the testing plate 12 and is used to maneuver the testing plate 12 during loading and testing.

Figure 4:
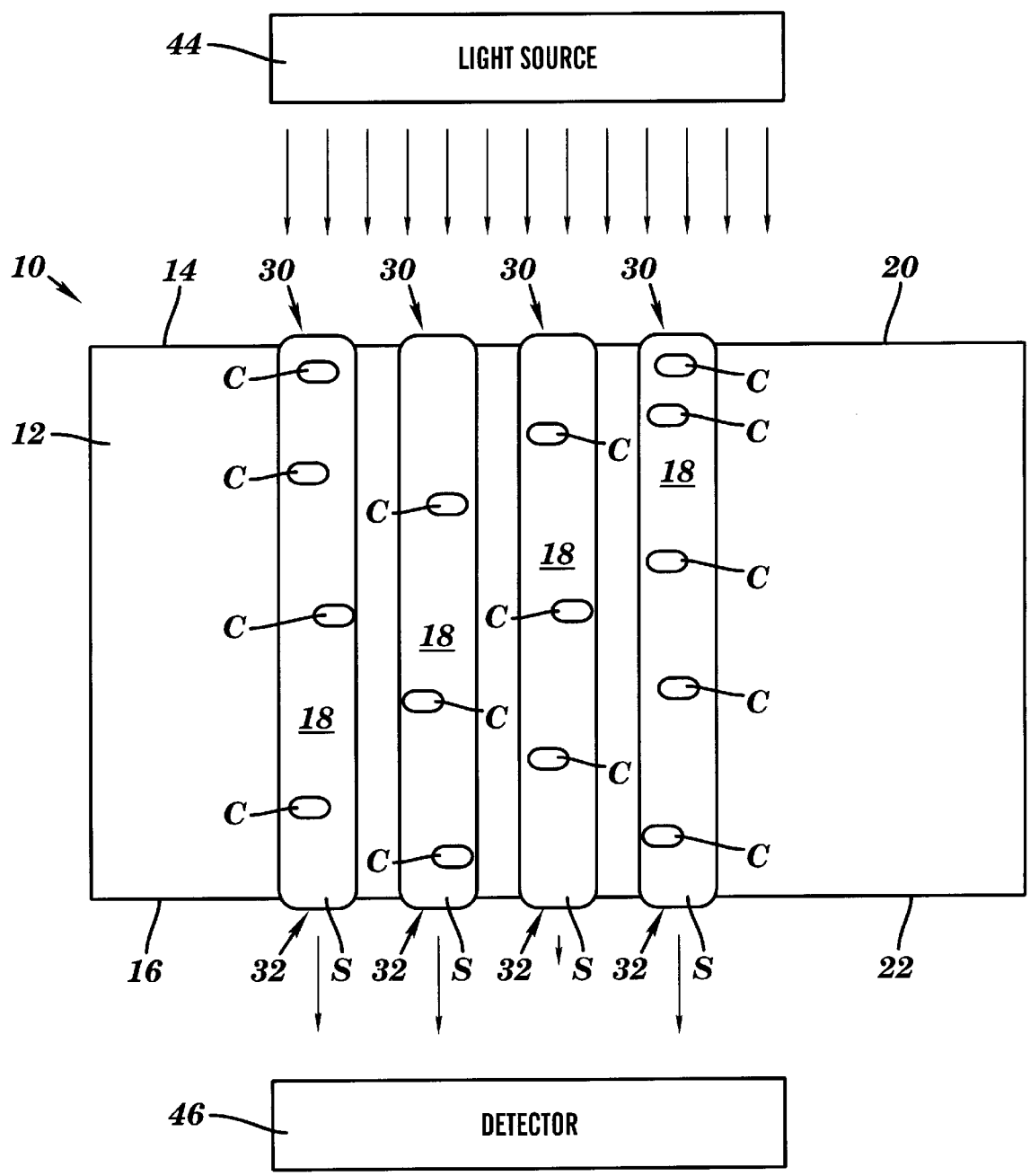
FIG. 4 is a block diagram of a testing apparatus with a multi-through hole testing plate in accordance with another embodiment of the present invention.

A plurality of through holes 18 are located in the testing plate 12. The holes 18 extend from openings 30 in the recessed portion 20 of one of the opposing surfaces 14 to openings 32 in the recessed portion 22 of the other opposing surface 16. In this particular embodiment, the holes 18 have a substantially cylindrical shape, although the holes 18 could have other shapes, such as a hexagonal cross-sectional shape or a cone shape. In this particular embodiment, each of the holes 18 has a diameter of about one millimeter and can hold about 5.5 microliters of solutions S and cells C, although the diameter, volume and number of cells C each hole 18 can hold can vary as needed or desired. The solution S along with cells C in the solution S are held in the holes 18 by surface tension as shown in FIG. 4. More specifically, the size of the holes 18 may need to change depending upon the solution S to be analyzed and that solution's surface tension properties. For example as understood by one of ordinary skill in the art, a buffer solution might have different surface tension properties than a culture media containing salt. There must be sufficient surface tension to keep the samples of solution S in the holes 18.

One of the advantages of the present invention is that the testing plate 12 is easy to manufacture. A plate of non-transparent material merely needs to have one recessed portion 20 or 22 formed in one of the opposing surfaces 14 or 16 and then the appropriate number of holes 18 needed to be drilled in the recessed portion 20 or 22 and through the plate 12. Since the holes 18 extend all of the way through, there is no need for a transparent bottom in each hole 18. Light transmitted into the holes 18 will pass through during testing. With prior wells, the testing apparatus also needed to be non-transparent, but since the wells did not extend through the apparatus, the bottom of the wells needed to be made of a transparent material to permit light to pass through the sample for optical analysis. Constructing these prior testing apparatuses was difficult and expensive.

Referring to FIG. 1, the testing plate 12 has about two-thousand holes 18 which extend through from one opposing surface 14 to the other opposing surface 16, although the number of holes 18 can vary as needed or desired. To assist an operator in identifying a particular hole 18 in this particular embodiment the holes 18 are arranged in groups and sets of holes 18. Each group 24 contains at least two rows and two columns of holes 18 and each set 26 includes at least two rows and two columns of groups 24. In this particular embodiment, each group 24 of holes 18 has five rows and five columns of holes 18 and there are eighty groups 24 of twenty-five holes 18 in this example, although the number can vary as needed or desired. The holes 18 in this example are spaced about 1.5 mm apart between rows of holes 18 and between columns of holes 18 within each group 24, although this distance can vary and the spacing between rows of holes 18 and columns of holes 18 within each group 24 can be different as needed or desired. In this particular embodiment, each set of groups 24 includes two rows of groups 24 and ten rows of groups 24 and there are four sets 26 which contain twenty groups 24 of holes 18 each in this example, although the number can vary as needed or desired. The groups 24 within a set 26 in this example are spaced about 2.0 mm apart and the sets 26 of groups 24 of holes 18 in this example are spaced about 2.5 mm apart, although these distances can vary as needed or desired.

By arranging the holes 18 in sets 26 and groups 24, it is much easier for an operator to identify a particular hole 18 in the testing plate 12 and retrieve a particular sample. The sets 26 of holes 18 help the operator identify the general area of the hole 18 and then the groups 24 help the operator to begin to narrow down the location of the hole 18. The column and row of the hole 18 in each group 24 provides the precise location of the hole 18. The spacing between sets 26, groups 24, and rows and columns are different to make it visually easier for an operator to identify a particular hole 18. When the holes 18 are all spaced equidistantly apart, then it is more difficult to identify a particular hole 18 and it is easier for an operator to lose his/her place and select a sample from the wrong hole 18.

Figure 7:
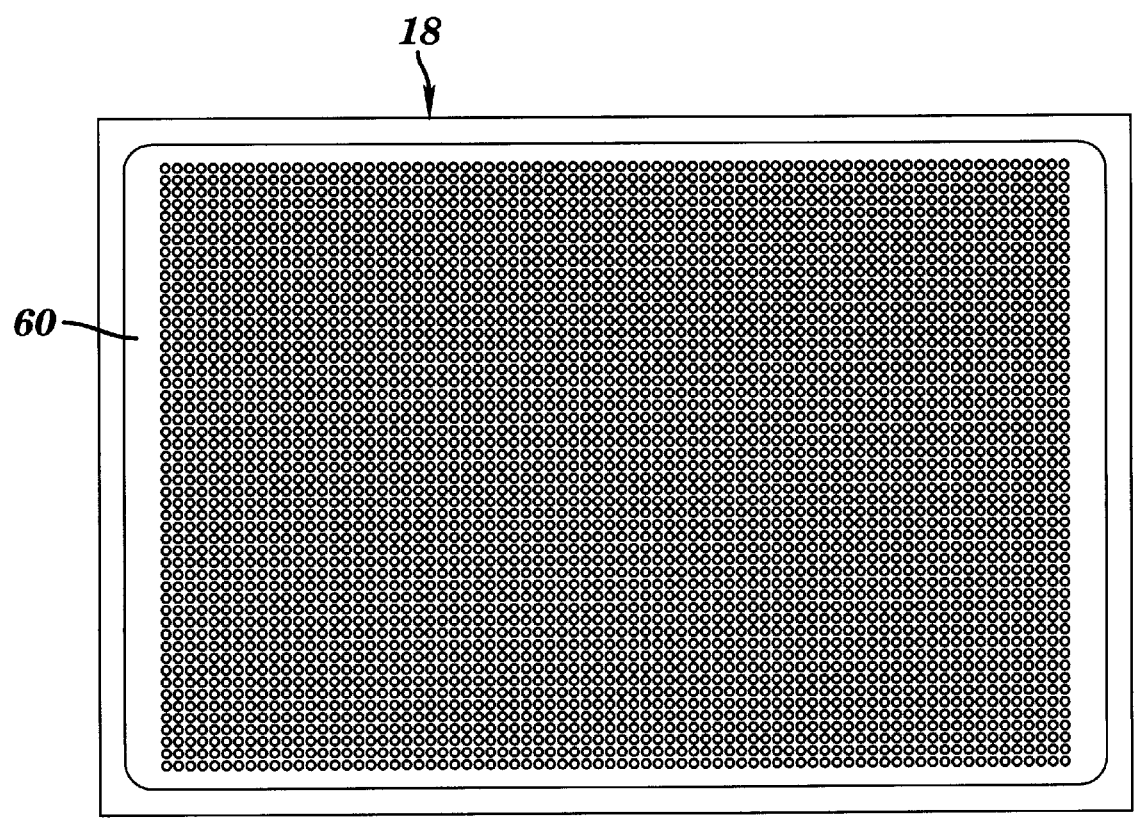
FIG. 7 is a top view of a multi-through hole testing plate in accordance with yet another embodiment of the present invention.

Although the holes 18 are arranged in groups 24 and sets 26 in testing apparatuses 10 and 50 to aid human operators, other arrangements for the holes 18 may also be used. For example, when the testing apparatuses are used by robotics, instead of human operators, the holes 18 can also be spaced equidistantly apart as shown in the embodiment of the testing apparatus 60 illustrated in FIG. 7. The testing apparatus 60 is identical to the testing apparatuses 10 and 50 described and illustrated earlier except for the that the holes 18 are equidistantly spaced apart.

Referring to FIG. 3, the testing apparatus 10 may also include a pair of optional evaporation plates 40 and 42. The evaporation plates 40 and 42 are each secured to the one of the opposing surfaces 14 and 16 of the testing plate 10. The evaporation plates 40 and 42 are secured to the testing plate 12 by bolts, clamps, or other mechanical means. When the evaporation plates 40 and 42 are secured to the testing plate 12 over the recessed portions 20 and 22, the recessed portions 20 and 22 in the opposing surfaces 14 and 16 of the testing plate 12 still space the openings 30 and 32 of the through holes 18 away from the evaporation plates 40 and 42. The evaporation plates 40 and 42 help to preserve the samples of solution S in the holes 18 in the testing plate 12 from evaporation and contamination.

One example of one application of the present invention will be discussed with reference to testing apparatus 10 shown in FIGS. 1–4. In this particular example, cells C are mutagenized using ultraviolet, chemical mutagenesis, or other mutagenesis technology. The cells C are grown to allow for segregation. Once the cells C have grown, the cells C are diluted to one cell C per ten microliters in a medium containing a fluorgenic or chromogenic substrate. For purposes of this example, the medium with the cells C is referred to as the solution S. As a result, the cells will be randomly distributed in the holes 18 and many of the holes 18 will contain one or more cells C.

Although one example of preparing the solution S and cells C is disclosed, other methods and techniques for preparing samples to be used with the testing apparatus 10 can be used as is readily understood by one of ordinary skill in the art.

Next, a testing plate 12 with a pair of opposing surfaces 14 and 16 and a plurality of holes 18 which extend from one of the opposing surfaces 14 to the other one of the opposing surfaces 16 is provided. At least one of the opposing surfaces 14 of the testing plate is immersed in the prepared solution S. The solution S enters openings 30 and 32 for each of the holes 18 in testing plate 12 and any gases in the holes 18 may escape through openings 30 and 32 at the opposite end of the holes 18. Alternatively, the testing plate 12 may be flooded with solution S so that the solution S enters through the top opening 30 to each hole 18.

One of the advantages of the present invention is the ease with which solution S can be loaded into each of the holes 18. As illustrated in the description above, all of the holes 18 in the testing plate 12 can be loaded with samples of solution S in a relatively short period of time and without any type of specialized solution delivery system. Prior testing apparatuses with wells required specialized solution delivery system, such as large pipette devices, to be able to load solution into each of the wells. These specialized solution delivery systems are difficult to use and are expensive.

Once the solution S has been drawn into the holes 18, the testing plate 12 is removed from the solution S. Surface tension holds the solution S in each of the holes 18. In this particular embodiment, each hole 18 has a diameter of about one millimeter and holds about 5.5 microliters of solution S and cells C as shown in FIG. 4, although the diameter and volume of each hole 18 can vary as needed or desired for the particular application. The handle 36 can be used to manipulate the position of the testing plate 12 during the above-described operations.

Once the testing plate 12 is removed from the solution S, the testing plate 12 can be placed on a supporting surface 28. Since the holes 18 are located in a recessed portion 22 of the testing plate 12, the openings 22 to the holes 18 are spaced from the supporting surface 28 so that any solution S being held by surface tension remains in the holes 18. A pair of evaporation plates 40 and 42 may be attached to the opposing surfaces 14 and 16 of the testing plate 12 to prevent the samples of solution S in the testing plate 12 from evaporating or becoming contaminated.

In this particular example, the testing plate 12 is then optionally incubated at a controlled temperature of about 37° C. and a humidity of about 70%, although the temperature and humidity will vary based upon the particular application. During the incubation, the cells multiply and produce a protein of interest (the cells could produce an enzyme, an antibody, or a metabolite which could be of interest). The ability of the protein, such as an enzyme, to hydrolyze a substrate is analyzed, such as by measurement of fluorogenic or chromogenic groups liberated by the hydrolysis.

Although one example of processing the samples of solution S in the testing plate 12 is disclosed, other methods and techniques for processing and analysis the samples can also be used and are know to those of ordinary skill in the art.

Next, in this particular example the samples of solution S with cells C in the holes 18 (as shown in FIG. 4) are tested using an image analyzer with a light source 44 and a detector 46 in this particular example. Light is transmitted from the light source 44 towards the openings 30 for the holes 18 in the testing plate 12 and through the solution S in the holes 18 of the testing plate 12. The detector 46 is positioned on the opposing side of the testing plate 12 and detects the light which has been transmitted through the solution S in the holes 18. Based upon the changes in the detected light from the transmitted light, information about the characteristics of the particular samples of solution S can be determined in a manner well known to those of ordinary skill in the art. In this particular example, the image analyzer is able to determine which holes 18 contain solution S with the highest concentration of converted substrate and consequently the highest amount of enzyme. The target in this case is to retrieve the cells C which produced the largest amount of enzyme. In a similar way, cells C which produced the largest amount of a protein or a chemical of interest could be identified.

Although one example of analyzing the samples of solution S in the testing plate 12 using optics is disclosed, other methods and techniques for analyzing the samples, such as non-optical methods, can also be used. For example, a plate containing samples of solution S with cells C could be blotted onto a membrane and used for performing Western blot analysis or alternatively, the samples S with cells C could be blotted onto substrate containing material whereby modification of the substrate is measured visually. As a result, when non-optical means are used to analyze the samples of solution in the testing plate 12, the testing plate 12 can be made of a transparent material.

Next, in this particular example the operator retrieves the samples of solution S which contain the highest concentration of converted substrate. The holes 18 with the solution S with the highest concentration of converted substrate can be identified and located based upon which set 26 of groups 24, which group 24, and which row and column within each group 24 each identified hole 18 is located. One of the advantages of the present invention is the arrangement of the holes in groups 24 and sets 26 which enables an operator to easily identify a particular hole 18 on the testing plate 12. Once the desired samples are retrieved, the operator can conduct further analysis on those samples in manners well known to those of ordinary skill in the art.

Although one example of retrieving one or more of the samples of solution S in the testing plate 12 is disclosed, other methods and techniques for retrieving samples can also be used. For example, if robotics are used to located and retrieve a particular sample, a different testing apparatus, such as testing apparatus 60 shown in FIG. 7, could be used. The robotics would not need the holes 18 to be arranged in groups 24 and sets 26 of holes 18, although such an arrangement may even aid the robotics in identifying and retrieving the desired sample.

Having thus described the basic concept of the invention, it will be rather apparent to those skilled in the art that the foregoing detailed disclosure is intended to be presented by way of example only, and is not limiting. Various alternations, improvements, and modifications will occur and are intended to those skilled in the art, though not expressly stated herein. These alterations, improvements, and modifications are intended to be suggested hereby, and are within the spirit and scope of the invention. Accordingly, the invention is limited only by the following claims and equivalents thereto.

What is claimed is:

1. A method for holding solution, the method comprising:

providing a testing plate with a pair of opposing surfaces and a plurality of holes, each of the holes extending from one of the opposing surfaces to the other one of the opposing surfaces;

immersing at least one of the opposing surfaces of the testing plate in the solution, wherein a portion of the solution enters openings for each of the holes in the immersed opposing surface;

removing the testing plate from the solution, wherein surface tension holds some of the solution in each of the holes; and supporting the opposing surfaces of the testing plate above a supporting surface.

2. The method as set forth in claim 1 wherein each of the holes is sized to hold a plurality of cells in the portion of the solution being held by surface tension.

3. The method as set forth in claim 1 wherein the holes in the testing plate are arranged in groups, each of the groups comprises at least two rows and two columns of holes.

4. The method as set forth in claim 3 further comprising identifying the location of at least one of the holes based on the group in which the hole is located.

5. The method as set forth in claim 4 further comprising identifying a row and a column in the group for the identified hole.

6. The method as set forth in claim 3 wherein the groups of holes on the testing plate are arranged in sets, each of the sets comprising at least two rows and two columns of groups.

7. The method as set forth in claim 6 further comprising identifying the location of the hole based on the set in which the hole is located.

8. A method for identifying the location of at least one sample of a solution, the method comprising:

providing a testing plate with a pair of opposing surfaces and a plurality of holes, each of the holes extending from one of the opposing surfaces to the other one of the opposing surfaces, wherein the holes are arranged in groups, each of the groups comprising at least two rows and two columns of holes and wherein the solution is located in at least some of the holes;

identifying the solution in at least one hole and locating the identified hole based upon the group in which the hole is located.

9. The method as set forth in claim 8 further comprising identifying a row and a column in the group for the identified hole.

10. The method as set forth in claim 8 wherein the groups of holes on the testing plate are arranged in sets, each of the sets comprising at least two rows and two columns of groups of holes.

11. The method as set forth in claim 10 further comprising identifying the location of the hole based on the set in which the hole is located.

12. A plate for holding samples of a solution with cells for analysis, the plate comprising:

a platform having a pair of opposing surfaces; and a plurality of holes in the platform, each of the holes extending from an opening in one of the opposing surfaces in the platform to an opening in the other one of the opposing surfaces and each of the holes being sized to hold a plurality of the cells;

wherein a portion of at least one of the opposing surfaces where the holes are located is recessed so that the openings in the platform are spaced in from the opposing surface.

13. The plate as set forth in claim 12 wherein a portion of the other opposing surface where the holes are located is recessed.

14. The plate as set forth in claim 12 wherein a portion of the other opposing surface where the holes are located is protruding.

15. The plate as set forth in claim 12 wherein each of the holes is sized to hold a plurality of cells in the portion of the solution being held by surface tension.

16. The plate as set forth in claim 9 wherein the holes are arranged in groups on the substrate, each of the groups comprises at least two rows and two columns of holes.

17. The plate as set forth in claim 16 wherein the groups are arranged in sets, each of the sets including at least two rows and two columns of groups.

18. The plate as set forth in claim 17 wherein a first distance between the sets is different than a second distance between the groups, is different than a third distance between the holes in each of the rows, and is different than a fourth distance between the holes in each of the columns.

19. The plate as set forth in claim 18 wherein the third and fourth distances are substantially the same.

20. An apparatus for holding samples for analysis comprising:
    a plate with a pair of opposing surfaces; and
    a plurality of holes in the plate, each of the holes extending from one of the opposing surfaces to the other one of the opposing surfaces;
    wherein the holes are arranged in groups on the plate, each of the groups comprising at least two rows and two columns of holes.

21. The apparatus as set forth in claim 20 wherein the groups are arranged in sets, each of the sets including at least two rows and two columns of groups.

22. The apparatus as set forth in claim 21 wherein a first distance between the sets is different than a second distance between the groups, is different than a third distance between the holes in each of the rows, and is different than a fourth distance between the holes in each of the columns.

23. The apparatus as set forth in claim 22 wherein the third and fourth distances are substantially the same.

24. The apparatus as set forth in claim 20 wherein a portion of at least one of the opposing surfaces where the holes are located is recessed so that the openings in the testing plate are spaced in from the opposing surface.

25. The apparatus as set forth in claim 20 wherein each of the holes is sized to hold a plurality of the cells which are suspended in the solution.

26. The apparatus as set forth in claim 25 wherein each of the holes holds between about 0.1 microliters and 10 microliters of the solution.

27. The apparatus as set forth in claim 20 further comprising a handle connected to the testing plate.

28. A method for analyzing a solution, the method comprising:
    preparing the solution of the sample for screening;
    providing a testing plate with a pair of opposing surfaces and a plurality of holes, each of the holes extending from one of the opposing surfaces to the other one of the opposing surfaces;
    immersing at least one of the opposing surfaces of the testing plate in a solution, wherein a portion of the solution enters openings for each of the holes in the immersed opposing surface;
    removing the testing plate from the solution, wherein surface tension holds some of the solution in each of the holes; and
    analyzing the solution in one or more of the holes.

29. The method as set forth in claim 28 wherein the step of analyzing is an optical analysis of the solution in one or more of the holes.

30. The method as set forth in claim 28 wherein the step of analyzing is a non-optical analysis of the solution in one or more of the holes.

31. The method as set forth in claim 1 further comprising analyzing the solution being held in at least one of the holes.

* * * * *

UNITED STATES PATENT AND TRADEMARK OFFICE
CERTIFICATE OF CORRECTION

PATENT NO. : 6,027,873
DATED : February 22, 2000
INVENTOR(S) : Volker Schellenberger and Amy Deming Liu It is certified that error appears in the above-identified patent and that said Letters Patent are hereby corrected as shown below:

On the title page, item [75], please change "Amy Deming Lui" to --Amy Deming Liu--.

Signed and Sealed this

Fifteenth Day of May, 2001

Attest:

NICHOLAS P. GODICI

Attesting Officer      *Acting Director of the United States Patent and Trademark Office*